US005092376A

United States Patent [19]

Blankenship et al.

[11] Patent Number: 5,092,376

[45] Date of Patent: Mar. 3, 1992

[54] APPARATUS FOR INJECTING RESIN

[75] Inventors: Tom Blankenship, Marthasville, Mo.; Ralph Compton, Granite City, Ill.; John Griffin, Ballwin, Mo.

[73] Assignee: McDonnell Douglas Corporation, St. Louis, Mo.

[21] Appl. No.: 632,926

[22] Filed: Dec. 24, 1990

[51] Int. Cl.[5] .......................... A61M 5/46; B65B 3/14

[52] U.S. Cl. .......................... 141/25; 141/21; 141/27; 604/117

[58] Field of Search .......................... 141/26, 27, 329, 21, 141/25; 222/326, 373, 389; 604/117, 140, 141

[56] References Cited

U.S. PATENT DOCUMENTS

| | | | |
|---|---|---|---|
| 2,578,812 | 12/1951 | Kollsman | 604/117 |
| 4,231,368 | 11/1980 | Becker | 604/117 X |
| 4,388,591 | 6/1983 | Lannan | 141/329 X |
| 4,635,827 | 1/1987 | Roedig | 222/160 |

FOREIGN PATENT DOCUMENTS

| | | | |
|---|---|---|---|
| 911778 | 12/1972 | Canada | 222/389 |
| 1358456 | 7/1974 | United Kingdom | 222/389 |
| 2208682 | 4/1989 | United Kingdom | 222/326 |

*Primary Examiner*—William A. Cuchlinski, Jr.
*Assistant Examiner*—W. Morris Worth
*Attorney, Agent, or Firm*—Benjamin Hudson, Jr.; Guy R. Gosnell; Timothy H. Courson

[57] ABSTRACT

There is provided by this invention an apparatus for injecting resin which provides a sealed injection position for uniform injection pressure on the resin and allows the depth of the injection needle to the controlled so that even minute delaminations, cracks, and voids in composite structures may be filled. The filling resin is contained in a syringe which is held in an injector frame. The syringe's needle protrudes from the nosepiece which is threadably engaged in the injector frame so that by further rotation of the nosepiece the depth of injection may be altered. Air lines and inlet ports are provided to urge the plunger of the syringe forward so as to eject resin into the composite structure, as well as to provide an improved seal about the injection position at the surface of the composite structure.

3 Claims, 1 Drawing Sheet

FIG. 1.
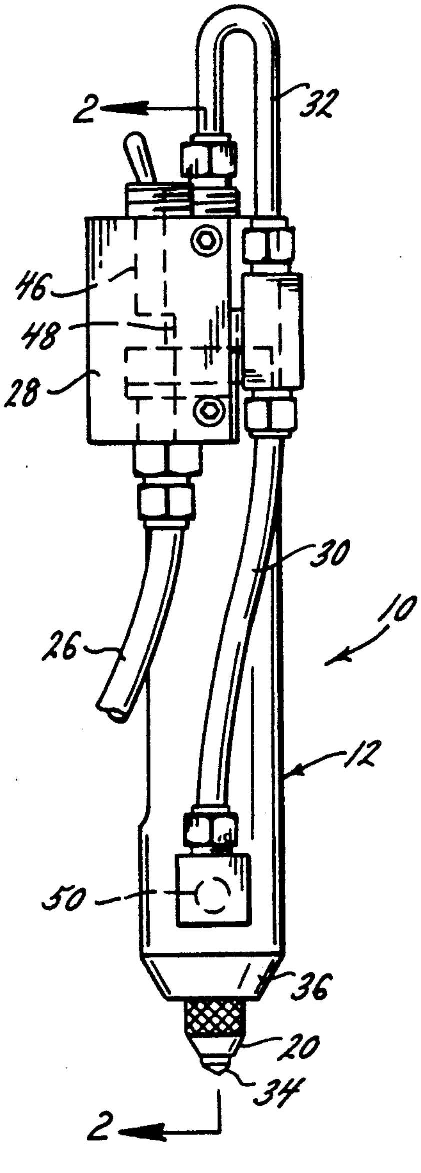
FIG. 2.
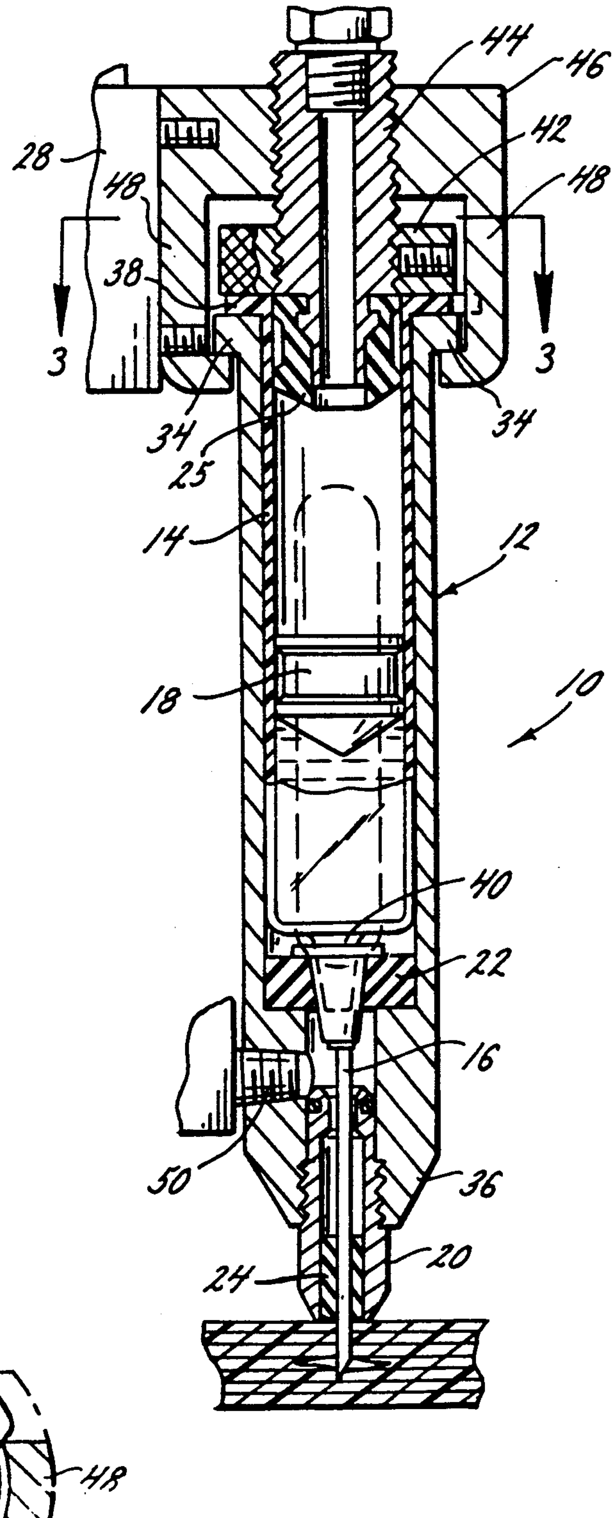
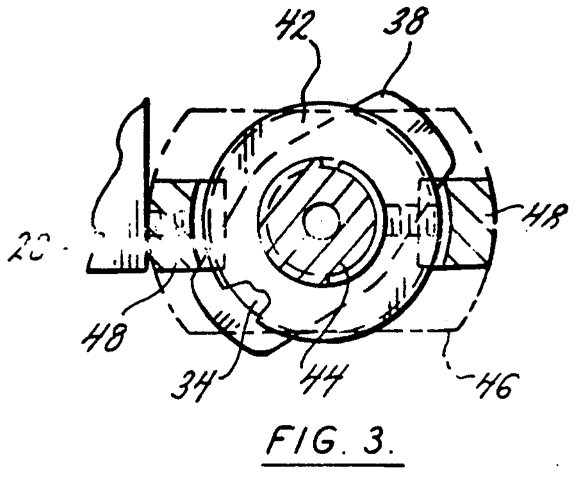
FIG. 3.

APPARATUS FOR INJECTING RESIN

BACKGROUND OF THE INVENTION

1. Field of the Invention

The present invention relates generally to an apparatus for injecting resin for use in repairing composite structures and more particularly to an apparatus that is capable of injecting resin, which is maintained under uniform pressure conditions, into a composite structure at a controlled depth.

2. Description of the Prior Art

In composite structures, defects such as delaminations, cracks, and voids may exist which substantially weaken the material. In order to correct such defects, uncured resin material may be introduced into the cured composite structure to fill the delamination, crack, or void.

A typical apparatus for injecting resin into the composite structure is a syringe and needle, filled with uncured resin material. The needle of such an apparatus is inserted into the composite structure and pressure is applied to the syringe by hand or by a mechanical clamp to inject the resin into the structure. An alternative apparatus for injecting resin into cured composite parts is an injection gun in which air pressure forces resin from a tube through a needle and into the composite structure.

Both the syringe and the injection gun suffer from several deficiencies including the lack of an effective seal around the composite injection position which results in nonuniform pressure on the filling resin so as to cause uneven application of the resin within the delamination, crack, or void. An additional deficiency is the lack of effective control of the depth of the injection needle delivering the resin. By not controlling the depth of the resin injection, the delamination, crack, or void may not be located, and thus not filled, by the prior art injection equipment.

It would be desirable to develop an apparatus for injecting resin which was capable of introducing resin into a composite structure at a controlled depth. It would be further desirable for the apparatus for injecting resin to maintain an effective seal around the composite injection position in order to insure that a uniform pressure is exerted on the filling resin.

SUMMARY OF THE INVENTION

There is provided by this invention an apparatus for injecting resin which provides a sealed injection position for uniform injection pressure on the resin and allows the depth of the injection needle to be controlled so that even minute delaminations, cracks, and voids in composite structures may be filled. The filling resin is contained in a syringe which is held in an injector frame. The syringe's needle protrudes from the nosepiece which is threadably engaged in the injector frame so that by further rotation of the nosepiece the depth of injection may be altered. Air lines and inlet ports are provided to urge the plunger of the syringe forward so as to eject resin into the composite structure, as well as to provide an improved seal about the injection position at the surface of the composite structure.

BRIEF DESCRIPTION OF THE DRAWINGS

FIG. 1 is a side view of an apparatus for injecting resin;

FIG. 2 is a side sectional view of an apparatus for injecting resin; and

FIG. 3 is a top sectional view of an apparatus for injecting resin.

DETAILED DESCRIPTION OF THE PREFERRED EMBODIMENT

The preferred embodiment of an apparatus for injecting resin 10, shown in FIG. 1, comprises an injector frame 12, a syringe 14, a needle 16, a plunger 18, a nosepiece 20, a syringe seal 22, a needle seal 24, and a rear seal 25. Additionally, air pressure is established by means of an external air supply which flows air through air input line 26 to an air on/off valve 28 which serves to control the air flow through a nosepiece air line 30 and a plunger air line 32.

The injector frame 12 has a hollow, cylindrical interior with an interior diameter that is only slightly larger than the external diameter of the syringe 14 so as to allow the syringe 14 to be slip-fit within the injector frame 12. The injector frame 12, which is open at both ends, has a first flanged end 34 through which the syringe 14 is inserted and a second tapered end 36 through which the syringe needle 16 may protrude. The syringe 14, a hollow tube with openings at both ends, has a flanged end 38 through which the plunger 18 is inserted and a tip 40 to which the needle 16 is connected.

Prior to the syringe's placement in the injector frame 12, the needle 16 is placed on the tip 40 of the syringe 14 by slipping the enlarged end of the needle 16 over the tip 40 of the syringe 14. Additionally, the syringe seal 22 is placed on the tip 40 of the syringe 14. The syringe seal 22 is typically composed of rubber and is in a circular shape with an interior diameter that is approximately equivalent to the exterior diameter of the tip 40 of the syringe 14 and an exterior diameter that is approximately equivalent to the interior diameter of the injector frame 12.

Once, the needle 16 is attached and the syringe 14 has been placed in the injector frame 12, the nosepiece 20 is threadably connected to the tapered end 36 of the injector frame 12. The nosepiece 20 is a hollow cylinder having various lengths depending on the desired injection depth as hereinafter explained. The needle seal 24 is inserted in the nosepiece 20 with the needle 16 passing through a small passage located along the central axis of the cylindrical needle seal 24. The passage through the needle seal 24 has a diameter that is approximately equivalent to the diameter of the needle 16, while the external diameter of the needle seal 24 is approximately equivalent to the interior diameter of the nosepiece 20.

Following the loading of the syringe 14 with the appropriate filling resin, the plunger 18 is inserted in the flanged end 38 of the syringe. The flanged end 38 of the syringe is sealed with the rear seal 25 which is retained by a backplate 42. The backplate 42 is threadably engaged by a screw 44. The screw 44 is threaded through a fixture 46 having two L-shaped sides 48 which serve to retain the flanged ends of both the injector frame 12 and the syringe 14. The screw 44 is threaded through the fixture 46 such that the backplate 42 contacts the rear of the syringe 14 and the rear seal 25 fills the opening at the rear of the syringe 14.

The screw 44 has a interior cylindrical bore along the axis about which it is rotated. The cylindrical bore is aligned with the cylindrical air passages of the backplate 42 and the rear seal 25 such that air entering the bore at one end of the screw 44 can exit through the air passages of the backplate 42 and the rear seal 25 so as to exert pressure on the plunger 18.

An external air source delivers air to the apparatus for injecting resin 10 by means of the air input line 26. The air input line 26 is coupled to the air on/off valve 28 which controls the flow of air to the apparatus for injecting resin 10. Air allowed to flow through the on/off valve 28 is coupled to both the nosepiece air line 30 and the plunger air line 32. The plunger air line 32 is connected to the screw 44 so that the air will flow through the bore of the screw 44 and the air passage of the backplate 42 so as to exert pressure on the plunger 18. Upon the application of air pressure, the plunger 18 is thus urged to move towards the tip 40 of the syringe 14 so as to push resin through the needle 16 and into the composite structure.

The nosepiece air line 30 is connected to the injector frame 12 through an air inlet port 50 on the injector frame 12. The air flowing through the nosepiece air line 30 and into the interior of the injector frame 12 forces the needle seal 24 to form a tight seal about the needle 16, nosepiece 20, and the surface of the composite structure. The air is forced from the air inlet port 50 towards the needle seal 24 due to the tight seal formed by the syringe seal 22 between the injector frame 12 and the syringe 14. The use of such air pressure and the syringe and needle seals serve to provide a sealed injection position for uniform injection pressure on the filling resin.

The depth of the injection is controlled by the nosepiece 20 which is threadably engaged in the tapered end 36 of the injector frame 12. The nosepiece 20 is screwed into the injector frame 12 such that the length of the needle 16 which extends beyond the nosepiece is equal to depth of injection desired. Thus, the depth of injection may be increased by further screwing of the nosepiece 20 into the injector frame 12, or the depth of injection may be decreased by partially unscrewing the nosepiece 20 from the injector frame 12.

Although there has been illustrated and described specific detail and structure of operations, it is clearly understood that changes and modifications may be readily made therein by those skilled in the art without departing from the spirit and the scope of the invention.

We claim:

1. An apparatus for injecting resin into a composite structure, comprising:
 a) a syringe having a first end and a second end;
 b) a needle attached to the first end of the syringe;
 c) a plunger means inserted in the second end of the syringe;
 d) a means for holding the syringe such that the needle protrudes through a first end of the holding means;
 e) a means for applying pressure to the plunger means such that the plunger means is urged toward the first end of the syringe;
 f) a means for controlling the depth of resin injection threadably engaged to the first end of the holding means such that the needle protrudes through the depth controlling means
 g) a first sealant means positioned about the needle such that a seal is maintained between the needle, the depth controlling means, and a workpiece; and
 h) a second sealant means positioned about the first end of the syringe such that a seal is maintained between the syringe, the needle and the holding means.

2. An apparatus for injecting resin into a composite structure, as recited in claim 1, wherein the holding means has an air inlet port positioned between the first sealant means and the second sealant means.

3. An apparatus for injecting resin into a composite structure, as recited in claim 2, further comprising a means for applying pressure to the holding means through the air inlet port such that the first sealant means are held in a sealed position.

* * * * *

UNITED STATES PATENT AND TRADEMARK OFFICE
CERTIFICATE OF CORRECTION

PATENT NO. : 5,092,376

DATED : March 3, 1992

INVENTOR(S) : Blankenship. et al

It is certified that error appears in the above-identified patent and that said Letters Patent is hereby corrected as shown below:

On the title page listing of the inventors, delete "Griffin" and substitute therefore -- Griffith --.

Signed and Sealed this

Eleventh Day of May, 1993

*Attest:*

MICHAEL K. KIRK

*Attesting Officer*

*Acting Commissioner of Patents and Trademarks*